US010076657B2

(12) United States Patent
Oster et al.

(10) Patent No.: US 10,076,657 B2
(45) Date of Patent: Sep. 18, 2018

(54) LEAD END HAVING SLOTTED MEMBER

(71) Applicant: Medtronic, Inc., Minneapolis, MN (US)

(72) Inventors: Daniel C. Oster, Blaine, MN (US); Rodney J. Haberte, Zimmerman, MN (US); Jeffrey M. Novotny, Wyoming, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 429 days.

(21) Appl. No.: 14/354,441

(22) PCT Filed: Oct. 19, 2012

(86) PCT No.: PCT/US2012/060988
§ 371 (c)(1),
(2) Date: Apr. 25, 2014

(87) PCT Pub. No.: WO2013/062863
PCT Pub. Date: May 2, 2013

(65) Prior Publication Data
US 2014/0309719 A1    Oct. 16, 2014

Related U.S. Application Data

(60) Provisional application No. 61/552,903, filed on Oct. 28, 2011.

(51) Int. Cl.
*A61N 1/05* (2006.01)
(52) U.S. Cl.
CPC ........... *A61N 1/05* (2013.01); *Y10T 29/49117* (2015.01)

(58) Field of Classification Search
CPC .............. A61B 2562/0209; A61B 5/04; A61B 2562/125; A61B 5/02427; A61B 5/683;
(Continued)

(56) References Cited

U.S. PATENT DOCUMENTS 5,458,629 A    10/1995    Baudino et al.
5,935,159 A    8/1999    Cross, Jr.
(Continued)

FOREIGN PATENT DOCUMENTS

WO    WO2008/060142    5/2008
WO    WO2013/062859    5/2013

OTHER PUBLICATIONS

PCT/US2012/060935: Search Report and Written Opinion dated Jan. 23, 2013.
(Continued)

*Primary Examiner* — Deborah Malamud
(74) *Attorney, Agent, or Firm* — Withers & Keys, LLC

(57) ABSTRACT

Various embodiments of this disclosure concern a lead end containing a slotted member. A slotted member can have a plurality of slots extending along at least a portion of the length of the slotted member, each of the slots having a respective positioning feature, the plurality of slots having a plurality of positioning features at different longitudinal positions along the length of the slotted member. The lead end can further include a plurality of conductors at least partially within the plurality of slots, each slot of the plurality of slots containing at least a respective one of the plurality of conductors, the plurality of conductors electrically connecting exposed electrical elements of both ends of the lead.

13 Claims, 10 Drawing Sheets

(58) Field of Classification Search
CPC .......... A61B 2560/0468; A61B 5/6813; A61B
5/6882; A61N 1/36125; A61N 1/3752;
A61N 1/375; A61N 1/0558; A61N 1/08;
A61N 1/00; A61N 1/04; A61N 1/0424;
A61N 1/0476; A61N 1/048; A61N
1/0488; A61N 1/0496; A61N 1/057;
A61N 1/059; A61N 1/303; A61N 1/3968;
A61H 2201/01; H01R 2201/12; H01R
24/58; Y10T 29/49002; Y10T 29/49117;
Y10T 29/49018
See application file for complete search history.

(56) References Cited

U.S. PATENT DOCUMENTS

| | | |
|---|---|---|
| 7,108,549 B2 | 9/2006 | Lyu et al. |
| 7,184,838 B2 | 2/2007 | Cross, Jr. |
| 7,184,840 B2 | 2/2007 | Stolz |
| 7,326,083 B2 | 2/2008 | Mehdizadeh et al. |
| 7,437,197 B2 | 10/2008 | Harris et al. |
| 7,499,755 B2 * | 3/2009 | Cross, Jr. ............. A61N 1/0553 607/117 |
| 7,680,544 B1 | 3/2010 | Conger |
| 7,797,057 B2 | 9/2010 | Harris |
| 2004/0097965 A1 | 5/2004 | Gardeski et al. |
| 2005/0182470 A1 | 8/2005 | Cross et al. |
| 2005/0234522 A1 | 10/2005 | Ley et al. |
| 2007/0168004 A1 | 7/2007 | Walter |
| 2009/0012591 A1 | 1/2009 | Barker |
| 2009/0143846 A1 | 6/2009 | Cross, Jr. |
| 2009/0222073 A1 | 9/2009 | Flowers et al. |
| 2009/0234407 A1 | 9/2009 | Hastings et al. |
| 2010/0305670 A1 | 12/2010 | Hall et al. |
| 2011/0022100 A1 | 1/2011 | Brase et al. |
| 2011/0072659 A1 | 3/2011 | Swanson et al. |
| 2011/0106189 A1 | 5/2011 | Seeley et al. |
| 2011/0165785 A1 | 7/2011 | Lindner et al. |
| 2011/0220408 A1 | 9/2011 | Walsh et al. |

OTHER PUBLICATIONS

PCT/US2012/060988: Search Report and Written Opinion dated Jan. 31, 2013.

* cited by examiner

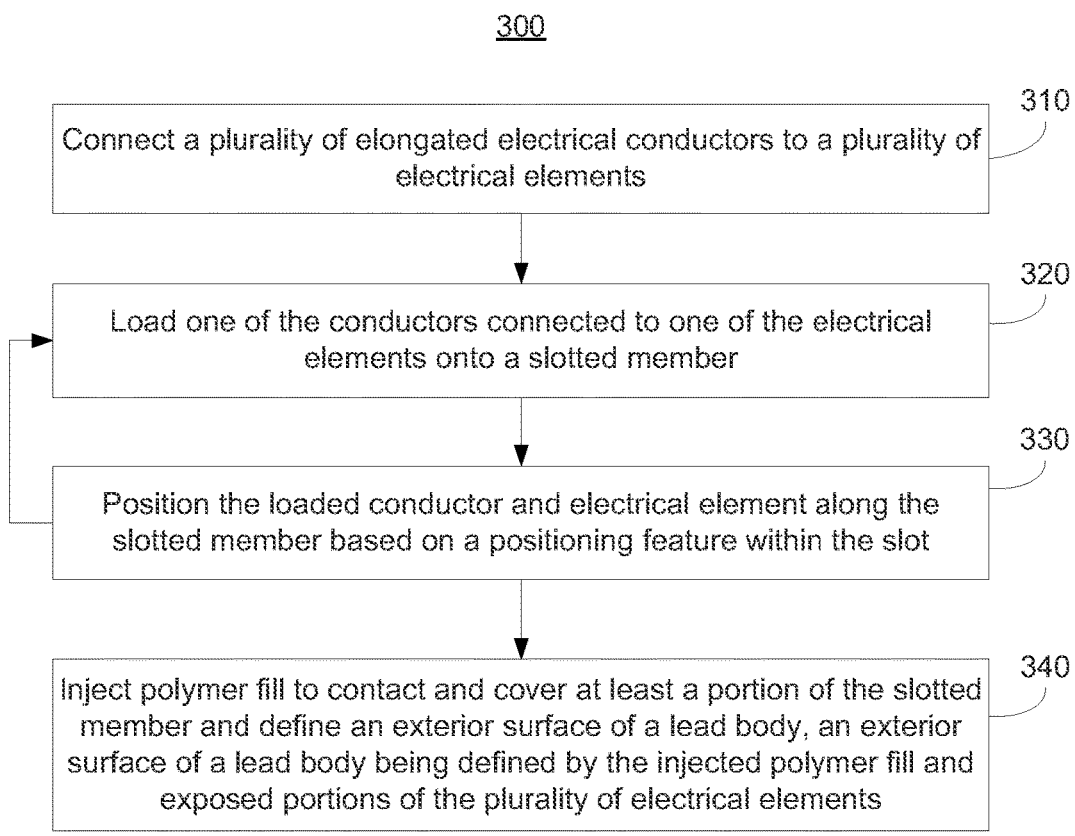

LEAD END HAVING SLOTTED MEMBER

TECHNICAL FIELD

The disclosure relates to medical leads, including implantable leads configured to conduct electrical energy between tissue and circuitry.

BACKGROUND OF THE INVENTION

Leads can be used to carry electrical energy between tissue and circuitry of a device, such as in sensing and/or stimulation applications. In the case of sensing, the electrical energy may be indicative of physiological activity while in a case of therapy delivery the electrical energy may comprise stimulation pulses. Leads may be partially or wholly implanted within a patient. For example, an implanted lead can carry electrical signals generated in a patient (e.g., by brain, heart, or muscles tissue) to signal processing circuitry in an implanted housing for data collection and/or determination of a patient state. Additionally or alternatively, electrical stimulation can be delivered from stimulation circuitry within the housing to a targeted area of the patient (e.g., brain, heart, spine, one or more nerves, pelvic floor, muscles) through the lead. Typically, the lead and the housing are separate components that are connected to one another during an implantation procedure.

SUMMARY

In general, this disclosure concerns implantable medical leads having a slotted member within one or both ends of the leads.

Various embodiments concern leads comprising a first end, a second end, and a main body between the first end and the second end, the first end having a first plurality of exposed electrical elements and the second end having a second plurality of exposed electrical elements. Such lead embodiments can further include a slotted member within the first end, the slotted member having a length and being longitudinally elongated along the length, the slotted member having a plurality of slots extending along at least a portion of the length of the slotted member and further having a plurality of positioning features, each slot having a respective positioning feature of the plurality of positioning features, each of the plurality of positioning features located at different longitudinal positions along the length of the slotted member. Such lead embodiments can further include a plurality of conductors at least partially within the plurality of slots, each slot of the plurality of slots containing at least a respective one of the plurality of conductors, the plurality of conductors electrically connecting at least some of the exposed electrical elements of the first plurality to at least some of the exposed electrical elements of the second plurality.

In various lead embodiments, the plurality of slots are arrayed around the circumference of the slotted member. In some cases, the plurality of slots are evenly spaced from each other around the circumference of the slotted member.

In some cases, a plurality of crimp sleeves connect the plurality of conductors to the first plurality of exposed electrical elements, the plurality of crimp sleeves at least partially within the plurality of slots. In various embodiments, the slotted member is tapered distally of the plurality of slots.

In some cases, the first end further comprises polymer fill encapsulating at least a portion of the slotted member, the polymer fill within at least some portions of the plurality of slots, the polymer fill deposited by injection molding. The polymer fill may define at least some of the exterior surface of the first end between the exposed electrical elements of the first end. Each exposed electrical element of the first end may comprise a ring that defines at least some of the exterior surface of the first end. In some cases, each ring of the first end comprises multiple holes through the exterior of the ring to the interior of the ring, the polymer fill at least partially within one of the holes. The holes may be dimensioned to accommodate a pin of an injection molding die, engagement of the pin with the hole securing the ring within the injection molding die during injection of the polymer fill.

In some of the lead embodiments, the first end is configured to plug into an implantable medical device and the exposed electrical elements of the first end are spaced to electrically connect with respective channels of the implantable medical device. The slotted member may provide a majority of the axial strength of the first end. A lumen may be within the first end and the main body, the lumen extending within the slotted member and open on the first end of the lead.

Various embodiments concern methods of making leads, the methods comprising connecting a plurality of elongated electrical conductors to a plurality of electrical elements and loading the plurality of conductors and the plurality of electrical elements onto a slotted member, the slotted member having a plurality of slots extending along at least a portion of the slotted member, the plurality of conductors being placed within the plurality of slots during the loading. Such method embodiments may further comprise positioning the plurality of electrical elements at different longitudinal locations along the slotted member based on a plurality of positioning features, the plurality of positioning features within the plurality of slots. Such method embodiments may further include injecting polymer fill to contact and cover at least a portion of the slotted member and define an exterior surface of a lead body, the polymer fill filling at least some portions of the plurality of slots, an exterior surface of a lead body being defined by the injected polymer fill and exposed portions of the plurality of electrical elements.

In some method embodiments, connecting the plurality of conductors to the plurality of electrical elements comprises mechanically and electrically coupling the plurality of conductors to the plurality of electrical elements with a plurality of coupling features. Positioning the plurality of electrical elements at different longitudinal locations along the slotted member may comprise sliding the plurality of coupling features within the plurality of slots. The coupling features may be crimp sleeves. The positioning features may facilitate the positioning of the plurality of electrical elements at different longitudinal locations along the slotted member by engagement between the plurality of positioning features and the plurality of coupling features. Each slot of the plurality of slots may contain a respective positioning feature of the plurality of positioning features and the plurality of positioning features may be respectively located at different longitudinal locations along the slotted member.

In various method embodiments, each electrical element of the plurality of electrical elements comprises a ring of a plurality of rings, and loading the plurality of conductors and the plurality of electrical elements onto the slotted member comprises sliding each ring of the plurality of rings over the slotted member. Each ring of the plurality of rings may comprise at least one hole through the exterior of the ring to the interior of the ring. Injecting polymer fill may comprise injecting polymer fill through one or more of the holes of the plurality of rings. Injecting polymer fill may comprise securing the plurality of rings within an injection molding die by penetration of a plurality of pins within the holes of the rings, each ring being penetrated by at least one pin during the injection of polymer fill. Each ring of the plurality of rings may comprise multiple holes through the exterior of the ring to the interior of the ring, each hole may be dimensioned to accommodate a pin of an injection molding die to secure the ring within the injection molding die during injection of polymer fill, and each hole may be dimensioned and configured to allow injection of polymer fill through the hole.

In various method embodiments, connecting the plurality of conductors to the plurality of electrical elements comprises one or both of crimping and welding. In some cases, each electrical element comprises a proximal end and a distal end, and the polymer fill is injected to directly contact each of proximal and distal ends of each electrical element to block the electrical elements from moving proximally or distally along the lead upon solidification of the polymer fill.

In some cases, the steps of loading and positioning are performed repeatedly for each of the plurality of conductors respectively connected to the plurality of electrical elements such that each pairing of a conductor connected to an electrical element is loaded and positioned on the slotted member before another pairing of another conductor connected to another electrical element is loaded and positioned on the slotted member. In various embodiments, the plurality of slots are evenly spaced from each other around the circumference of the slotted member.

The details of one or more examples are set forth in the accompanying drawings and the description below. Other features, objects, and advantages will be apparent from the description and drawings, and from the claims.

BRIEF DESCRIPTION OF THE FIGURES

FIG. 12 illustrates a flow chart of a method of making a lead end.

DETAILED DESCRIPTION OF THE INVENTION

Figure 1:
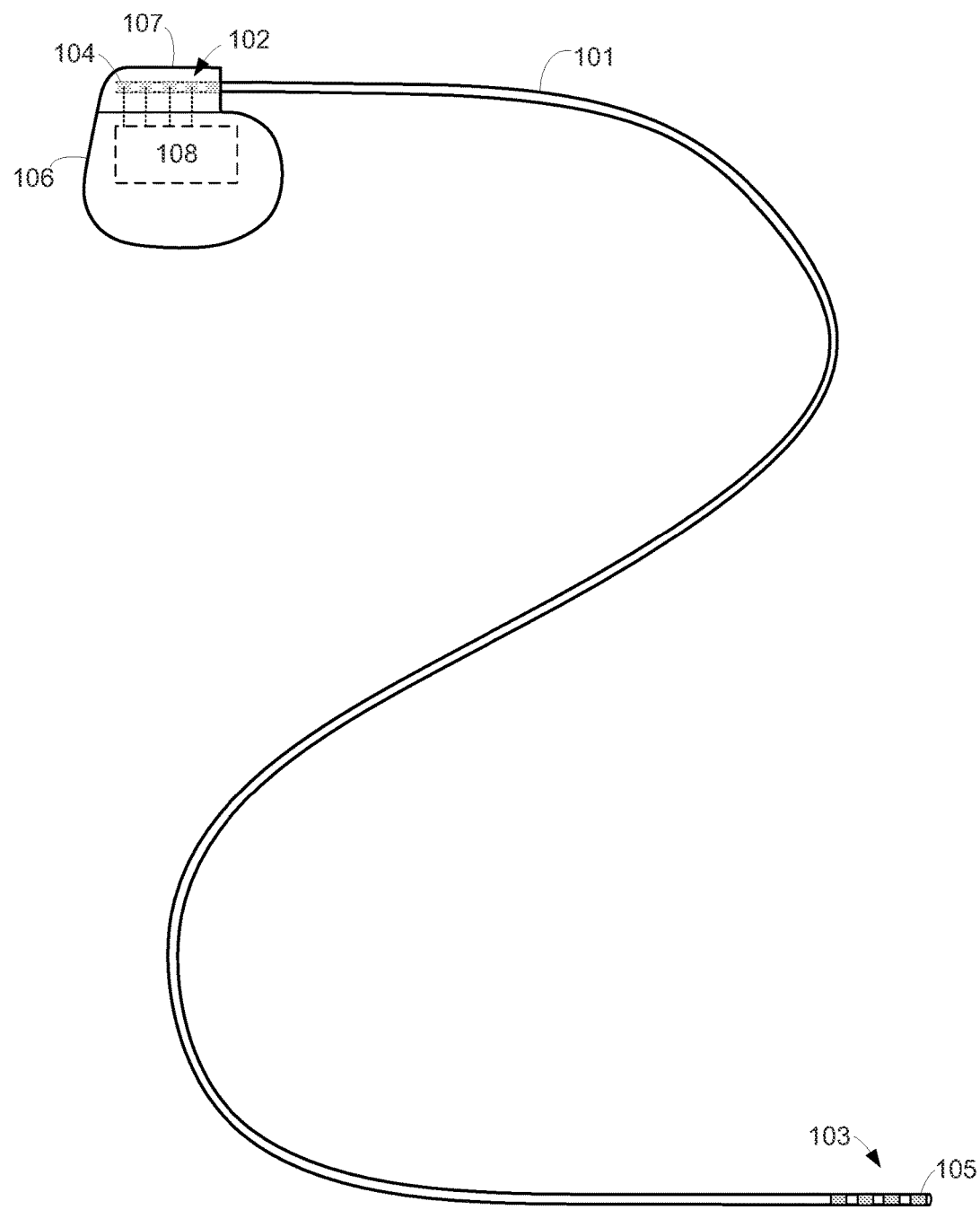
FIG. 1 illustrates an implantable lead and an implantable device for one or both of sensing signals and delivering stimulation.

FIG. 1 illustrates an implantable lead 101 plugged into an implantable medical device (IMD) 106. The lead 101 includes a proximal end 102 and a distal end 103. A number of electrodes are on the distal end 103 of the lead 101 (such as ring electrode 105) while a number of contacts are on the proximal end 102 of the lead 101 (such as contact ring 104). A plurality of conductors, which are not shown in FIG. 1 because they are fully contained within the body of the lead 101, electrically connect respective contacts of the proximal end 102 with electrodes of the distal end 103.

The IMD 106 can be configured for stimulating tissue (e.g., as a brain stimulator, spinal stimulator, peripheral nerve stimulator, pelvic nerve stimulator, cardiac stimulator, muscle stimulator, or any other type of stimulator configured to deliver electrical energy). The IMD 106 may additionally or alternatively be configured to sense one or more bioelectrical signals received by one or more electrodes and conducted through the lead 101 (e.g., nerve signals, local field potential signals, brain signals, cardiac signals, electromyogram signals, or any other physiologic signals).

When the proximal end 102 of the lead 101 is plugged into the header 107 of the IMD 106, electrical connections are made between conductors of the lead 101 and circuitry 108 of the IMD 106. Circuitry 108 may include signal processing circuitry, stimulation circuitry, a controller, memory, a power source, and/or a switch matrix, among other things. The electrical connections between the IMD 106 and the lead 101 are made by metal conductors within the header 107 of the IMD 106 touching respective contacts (e.g., contact 104) of the proximal end 102 of the lead 101. At least part of the proximal end 102 of the lead 101 is inserted into the header 107 to make the physical connections between the contacts of the lead 101 and the electrical conductors of the IMD 106. The exposed contacts of the proximal end 102 of the lead 101 are spaced to physically align and connect with different metal conductors within the header 107, each of the different metal conductors of the header 107 electrically connecting with different stimulation and/or sensing channels of the IMD 106.

The header 107 includes an opening to allow insertion of the proximal end 102 of the lead 101 into the header 107. In various embodiments, the opening is only slightly larger in diameter then the proximal end 102 of the lead to minimize the amount of space for bodily fluids to enter the header 107. Furthermore, one or more seals can be located within the header 107, around the proximal end 102 of the lead 101, to limit bodily fluids from shorting electrical circuits. Electrical signals are conducted between the header 107 and circuitry 108 by a feedthrough that bridges between the housing of the IMD 106 and the header 107.

The main body of the lead 101, which is between the proximal end 102 and the distal end 103 of the lead 101, is relatively flexible to allow the lead 101 to be implanted along curved paths within the body. Furthermore, flexibility of the main body allows the lead 101 to accommodate the movements of the body (e.g., along the neck or the back of a patient.

While it can be advantageous to have a relatively flexible main body of the lead 101, it can also be advantageous to have the proximal end 102 of the lead 101 be relatively stiff. Some resistance in inserting the proximal end 102 of the lead 101 into the header 107 can be experienced because of the close fit between the outer diameter of the proximal end 102 and the inner diameter of the space within the header 107. Moreover, resistance may be experienced as the proximal end 102 may have to overcome seals or other leakage barriers upon inserting the proximal end 102 into the header 107. Such resistance could risk kinking of the proximal end 102, slipping of the physician's grip on the proximal end 102, and/or uncertainly over whether the proximal end 102 is fully inserted within the header 107.

In some cases leads can be difficult to manufacture. The distal and proximal ends can have many components and the positioning and alignment of those components can be particularly important. For example, the contacts of the proximal end 102 should align with the spacing of the metal conductors within the header 107 so that each contact is electrically connected with a different channel of circuitry 108 of the IMD 106. Misalignment due to contact spacing errors on the proximal end 102 can cross channels or fail to electrically connect with a proper channel. Likewise, spacing of electrodes on the distal end 103 which fails to follow an intended design can compromise sensing and/or stimulation coverage.

The present disclosure concerns, among other things, implantable leads having an end that is built around a slotted member. The slotted member can facilitate quick and accurate placement of electrical elements, such as ring contacts and electrodes, at pre-spaced locations when constructing an end of a lead. In some embodiments, the slotted member can be a supportive member adding stiffness to an end of a lead. As discussed herein, a stiff proximal end 102 can more easily overcome obstacles (e.g., seals) resisting insertion, thereby facilitating easier insertion of the proximal end 102 into the header 107. A stiff proximal end 102 can also serve has a firm and robust handle for a physician in inserting the proximal end 102 into the header 107. Also, a stiff proximal end 102 can maintain its integrity during insertion, where a more flexible end may be too floppy or prone to kinking to quickly and confidently insert into the header 107 during an implantation procedure.

FIGS. 2-11 show various aspects for forming a proximal end of a lead, such as the proximal end 102 of the lead 101 of FIG. 1. It is noted that the techniques demonstrated in FIGS. 2-11 may be used to construct a distal end 103 of a lead 101.

Figure 2:
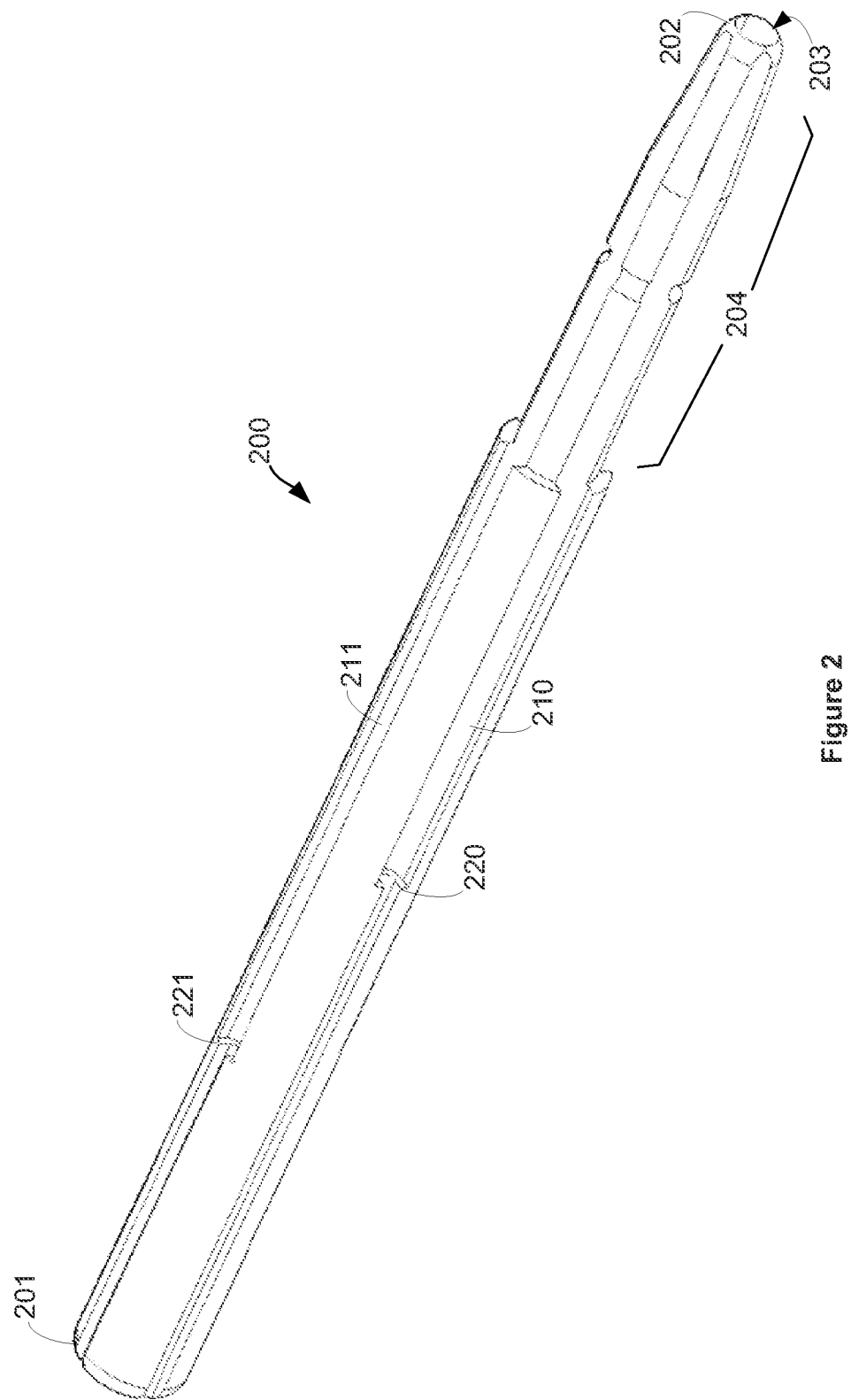
FIG. 2 illustrates an embodiment of a slotted member.

FIG. 2 illustrates a slotted member 200. The slotted member 200 is an elongated structure having a length. The slotted member 200 has a proximal end 201 and a distal end 202. In the embodiment of FIG. 2, the slotted member 200 has a lumen running the full length of the slotted member 200 as shown by lumen opening 203. In various embodiments, slotted member 200 may have no lumen or a lumen that only runs a partial length of the slotted member 200.

Slotted member 200 has multiple slots that run at least a partial length along the slotted member 200. The slotted member 200 of FIG. 2 has four slots, including slots 210 and 211 and two more slots on the underside of the slotted member 200. Slots can run the entire lengths of the slotted member 200, or may only run for some distance along the length of the slotted member 200. Any number of slots can be arrayed around a slotted member in various embodiments, such as one, two, three, four, five, eight, ten, twenty, etc. In various embodiments, slots are evenly arrayed around the periphery of the slotted member. In various embodiments, electrical elements (e.g., contacts or electrodes) are provided on a lead end in a number equal to the number of slots of a slotted member within the lead end.

Figure 4:
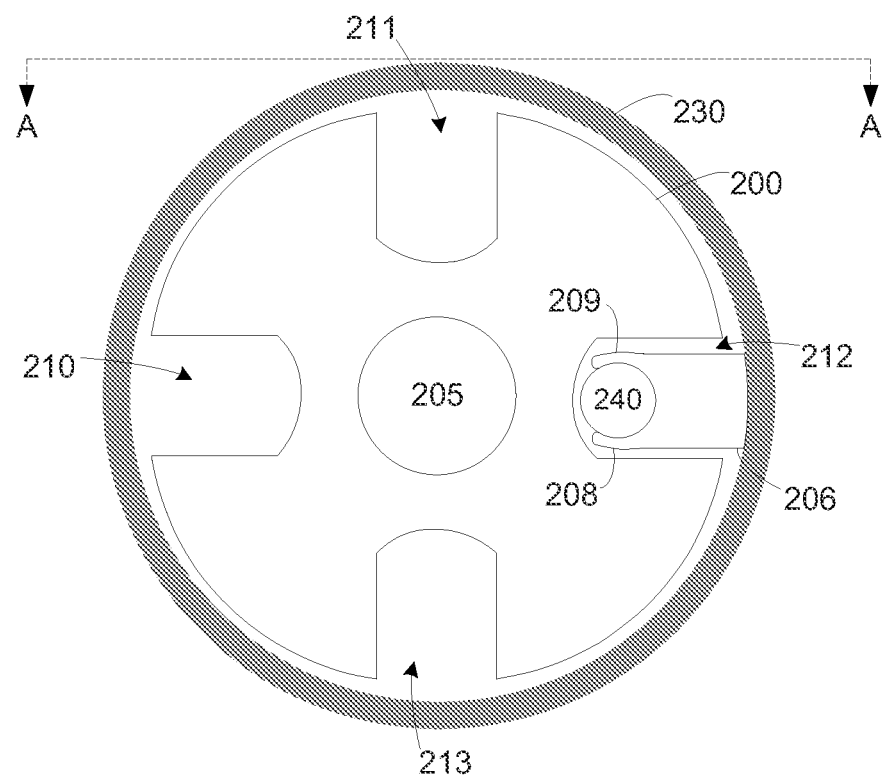
FIG. 4 illustrates a cross sectional view of a contact ring on a slotted member.

Slots, such as slots 210 and 211, are channels in a slotted member that are sized and otherwise configured to accommodate a conductor along a length of the slotted member 200. All four slots 210-213 of the slotted member 200 are shown in FIG. 4. In some embodiments, the slots are deep and wide enough that a conductor can run within a slot without extending out of the top of the slat (e.g., the depth of the slot is greater than the height of the conductor). In some embodiments, a conductor sitting as deeply within a slot as possible will still emerge from the top of the slot past the periphery of the slatted member 200 (e.g., the depth of the slot is less than the height of the conductor). In some embodiments, the depth of a slat changes along the length of the slot. For example, the depth of the slot may be greater than the height of the conductor at a proximal and/or midpoint of the slotted member 200 but the depth of the slot may be less than the height of the conductor at a distal section of the slotted member 200. In this way, a slot may become shallower in a distal direction and deeper in a distal direction. The changes in channel depth may be abrupt, as with a step, or gradual by sloping.

Slots 210 and 211, as well as the slots on the underside of the slotted member 200, run the entire length of the slotted member 200 but change in dimension along the length. For example, slot 210 includes positioning feature 220 and slot 211 includes positioning feature 221. The slots 210 and 211 have a step at each positioning features 220 and 221 making the slots 210 and 211 abruptly smaller. A positioning feature, as referred to herein, such as positioning features 220 and 221, is a restriction within a slot sized to block a component of a lead from moving in a direction along a slotted member. In the case of slots 210 and 211, positioning features 220 and 221 are restrictions within the slots 210 and 211 by decreasing the depth of the slots 210 and 211 proximal of the positioning features 220 and 221 and narrowing the slots 210 and 211 proximal of the positioning features 220 and 221. Steps at positioning features 220 and 221 are illustrated in FIG. 2 to show the decrease in slot depth and width, such that slot 210 is wider and deeper distally and shallower and narrower proximally and slot 211 is wider and deeper distally and shallower and narrower proximally (not including the taper 204). In some embodiments, positioning features are the ending points of slats, such that past a positioning feature the circumference of the slotted member 200 does not have a channel in line with the slot leading up to the positioning feature. As such, in some embodiments positioning features comprise points of termination of the slots, at which point the slots are no longer channels within the slotted member 200 (e.g., as if slot 210 ended at positioning feature 220 such that the slot 210 ran distally of the positioning feature 210 along the slotted member 200 but did not run proximally of the positioning feature 210 along the slotted member 200). Maintaining a portion of a slot that is narrow, as opposed to terminating a slot, can be useful in some embodiments because the smaller portion of the slot may be too small to accommodate a conductor but can nevertheless be filled with polymer fill from an injection molding process, as will be discussed further herein. These smaller slot sections can serve as grip features for polymer fill to grip and mechanically secure the slotted member 200.

Positioning features 220 and 221, as will be explained further herein, restrict the movement of one or more elements within the slots 210 and 211. The restriction in movement can facilitate the proper positioning of electrical elements along the slotted member 200, such as ring electrodes, because the movement of the ring electrodes can be limited if a portion of the ring electrodes, or something to which the ring electrodes are attached such as a crimp sleeve, engage with the positioning features 220 and 221. In some embodiments, positioning features can include bumps within a slot, tabs in the slot or the connector ring, machined geometry (e.g., utilizing key and key-hole fitting shapes).

Slotted members, such as slotted member 200, can be made in various ways. In some embodiments the slotted member is a unitary body. Various slotted members can be made from one or more materials. In some cases, a slotted member can be made solely from one type of material, such as a polymer material. In the case of a polymer slotted member, the slotted member can be formed in the same or comparable shape shown in FIG. 2 by injection molding or stereolithography. In some cases, a more generalized shape can be formed and then the shape can be machined, cut, or otherwise sculpted to form a desired shape, such as that of slotted member 200 shown in FIG. 2. For example, a tube or rod shape can be injection molded or extruded and then machined to form the slotted member 200 of FIG. 2.

It is noted that slotted member 200 includes a taper 204 that narrows the outer profile of the slotted member 200 distally. A taper 204 can be a more flexible section of the slotted member 200, the section being more flexible because it comprises less material. Taper 204 can be used as a strain relief, among other things.

Figure 3:
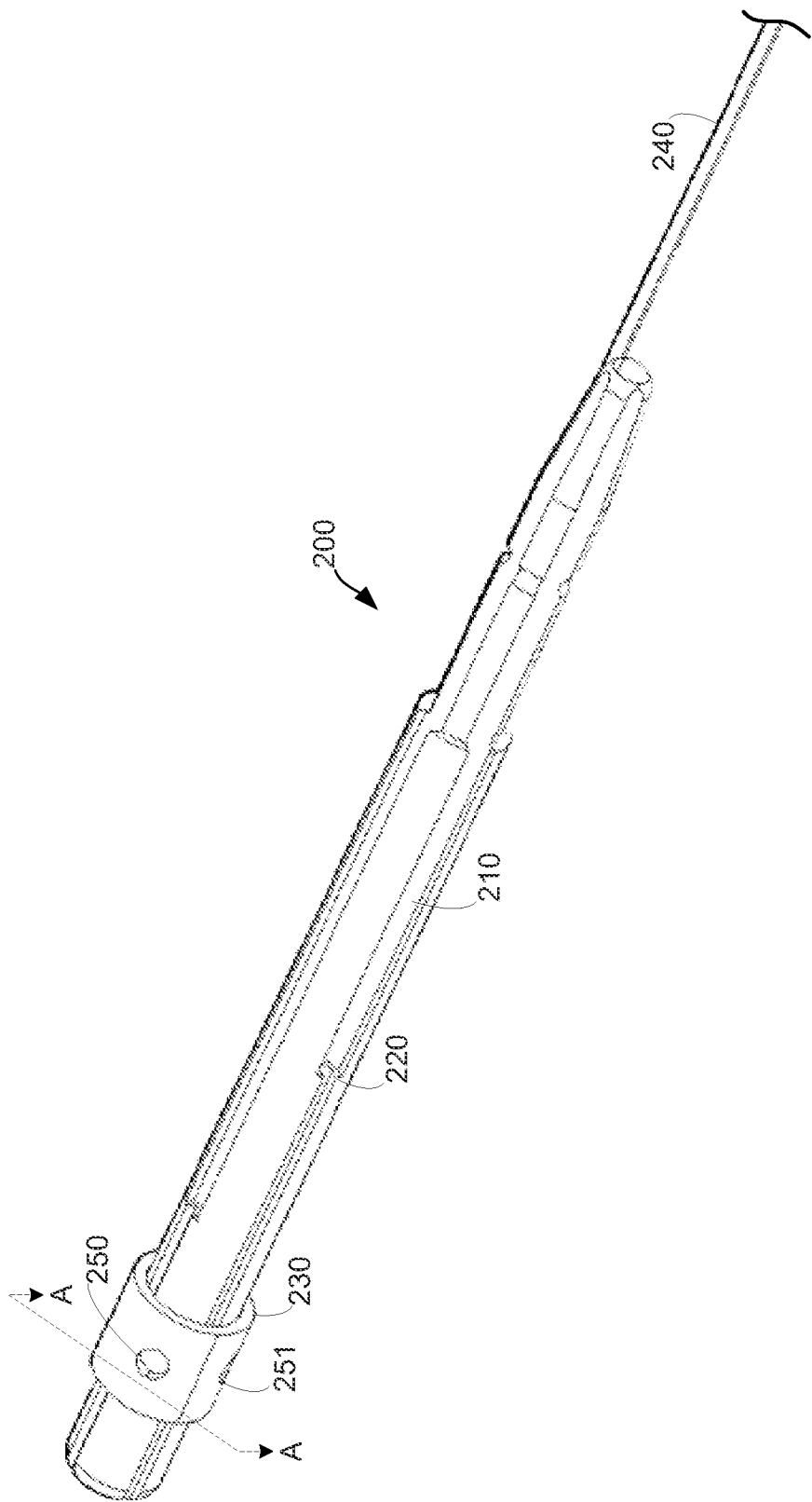
FIG. 3 illustrates a slotted member and a contact ring.

Electrical elements can be loaded onto the slotted strut 200. Electrical elements, as referred to herein, are metal lead components exposed on the exterior of a lead that are configured for receiving electrical energy into the lead and/or delivering electrical energy from the lead. Electrical elements include, but are not limited to, electrodes and contacts, such as ring electrodes, contact rings, segmented electrodes, segmented contacts, and partial rings. FIG. 3 illustrates a contact ring 230 and conductor 240 having been loaded onto the slotted member 200. Contact ring 230 includes at least two holes 250 and 251 (one or two more holes are provided on the underside of the contact ring 230 in various embodiments) that go from an exterior surface of the contact ring (e.g., an outer circumferential surface) to an interior surface of the contact ring 251 (e.g., an inner circumferential surface). The holes 250 and 251 can be used for securing the contact ring 230 within an injection molding die and/or as ports through which to inject polymer fill.

Although not shown in FIG. 3, the contact ring 230 is mechanically and electrically connected to conductor 240 by a coupling feature. In various embodiments the coupling feature is the crimp sleeve 206 shown in FIG. 4. The crimp sleeve 206 can crimp around the conductor 240. The crimp sleeve 206 can also be welded to the contact ring 230. A crimp sleeve may be welded within a slot of a contact ring 230, to the inside surface of the contact ring 230, or to another surface or area of the contact ring 230. In some other embodiments, the conductor 240 may be welded or otherwise attached directly to the contract ring 230.

FIG. 4 shows the cross sectional view of the AA cross section of FIG. 3, which includes the cross section of the contact ring 230, crimp sleeve 206, and slotted member 200. All four of the slots 210-213 of the slotted member 200 are shown in the cross sectional view of FIG. 4, as well as the lumen 205 of the slotted member 200. In particular, FIG. 4 shows contact ring 230 over the slotted member 200 while a crimp sleeve 206, welded to the contact ring 230, is within the slot 212. The crimp sleeve 206 is electrically and mechanically connected to the conductor 240 by arms 208 and 209 being pressed around the conductor 250 to bring conductive metal surfaces of the crimp sleeve 206 and the conductor 240 in contact with each other.

As shown in the AA cross section in FIG. 4, the crimp sleeve 206 is able to slide within the slot 212. The portion of the slot 212 illustrated in FIG. 4 is wide and deep enough to permit the subassembly of the contact ring 230, crimp sleeve 206, and conductor 240 to slide over the slotted member 200. Because the subassembly of the contact ring 230, crimp sleeve 206, and conductor 240 are attached to one another, the subassembly is rigid at least between the contact ring 230 and the crimp sleeve 206 (and in some cases the proximal end of the conductor 240). As shown in FIG. 4, a lock-and-key relationship is established between the outer profile of the slotted member 200 and the inner profile of the subassembly of the contact ring 230, crimp sleeve 206, and conductor 240. For example, the contact ring 230 could not rotate but for a few degrees because the contact ring 230 surrounds the slotted member 200 and the crimp sleeve 206 is within the slot 212. This lock-and-key relationship can prevent the contact ring 230 from rotating and thereby can maintain an angular position of the contact ring 230. As discussed further herein, one or more pins may penetrate one or more of the holes 250 and 251 within the contact ring 230 to further stabilize the contact ring 230 during injection molding. Accordingly, the lock-and-key relationship keeps electrical elements (e.g., contact ring 230) and in some cases holes of the electrical elements (e.g., holes 250 and 251) in an initial alignment that can match an arrangement of pins of an injection mold die and/or ports through which polymer fill is injected. Therefore, the presence of the crimp sleeve 206 or other feature within the slot 212 can maintain an alignment of the contact ring 230 and features on the contact ring 230, among other things.

It is noted that each of the slots 210-213 are at different angular positions around the slotted member 200. Specifically, the slots 210-213 are at 90 degree positions around the slotted member 200. In some embodiments, slots are evenly spaced around a slotted member, while in some other embodiments the slots are unevenly spaced. Spreading the slots 210-213 around the periphery of the slotted member 200 provides separation between conductors (e.g., conductors 240 and 241) within the slots 210-213. Such separation can help minimize the chance of an electrical short between conductors. The angular position of slots 210-213 around the slotted member 200 can also align holes (e.g., 250 and 251) with pins and/or injection ports of an injection molding die during placement of a subassembly (e.g., as in FIG. 8) in an injection mold die before and during injection molding. For example, once a crimp sleeve 206 is rigidly attached to the contact ring 230, the orientation of the holes 250 and 251 relative to the slotted member 200 is driven by the orientation of the slot 212. As such, the lock-and-key relationship between the slotted member 200 and the subassembly of the contact ring 230 and the crimp sleeve 206 can maintain the angular orientation of the holes 250 and 251 for later alignment with pins and/or injection ports of an injection molding die. In this way, a slotted member 200 can establish an initial pitch control of electrical elements and holes of the electrical elements.

During assembly, the contact ring 230 is placed over the distal end 202 of the slotted member 200 and slides proximally along the slotted member 200 as far as it can travel before the crimp sleeve 206 engages with the positioning feature 222. The positioning feature 222 engaging with the crimp sleeve 206 is illustrated in FIG. 5.

Figure 5:
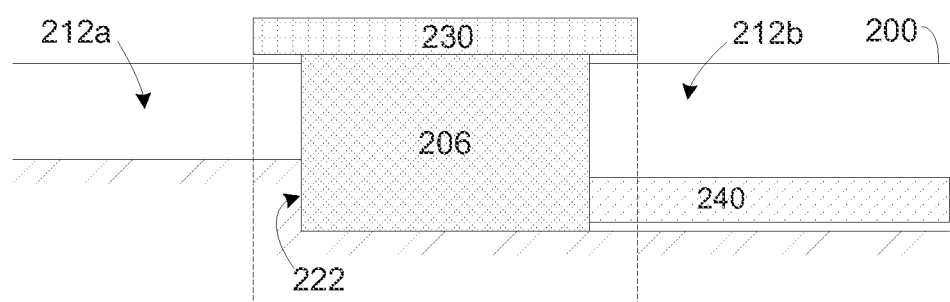
FIG. 5 illustrates a cropped cross sectional side view of a contact ring on a slotted member.

FIG. 5 illustrates a cropped cross sectional side view of the subassembly of the crimp sleeve 206, contact ring 230, and conductor 240. As shown in the cross sectional side view of FIG. 5, the crimp sleeve 206 is within the slot 212 and the depth of the slot 212 is deeper in the distal slot area 212b and shallower in the proximal slot area 212a. This change in depth forms the step of the positional feature 222 that is engaged with the crimp sleeve 206. This step blocks the crimp sleeve 206 from sliding further within the slot to the proximal slot area 212a. Being that the crimp sleeve 206 is welded to the inside of the contact ring 230 and mechanically attached to the conductor 240, the engagement between the crimp sleeve 206 and the positional feature 222 blocks the contact ring 230 and the conductor 240 from moving proximally along the slotted member 200. In this way, engagement between the crimp sleeve 206 and the positional feature 222 provides some support to keep the contact ring 230 at a pre-determined location along the slotted member 200. As multiple contact rings are stopped by respective positional features at different locations along the slotted member 200, the contact rings are positioned and supported in an array having a pre-determined spacing that aligns with electrical connectors within an IMD for connecting respective channels.

It is noted that the positional feature 222 of slot 212, shown in FIG. 5, is essentially identical to positioning feature 220 of slot 210 and positioning feature 221 of shot 211 shown in FIG. 2. As discussed herein, the positioning features 220-222 are restrictions within the slots 210-212. A crimp sleeve (or other feature) can be loaded into a slot and moved proximally within the slot until the crimp sleeve (or other feature) engages with a positioning feature blocking further proximal movement, positioning an electrical element at a pre-determined location along the slotted member. In various other embodiments, a crimp sleeve is not used or does not engage with a positioning feature. For example, in some embodiments a crimp sleeve is not used and instead the conductor or a feature of an electrical element (e.g., a feature projecting downward from the electrical element into the slot) engages with the positioning feature to block movement of the electrical element at a pre-determined location along the slotted member.

Figure 6:
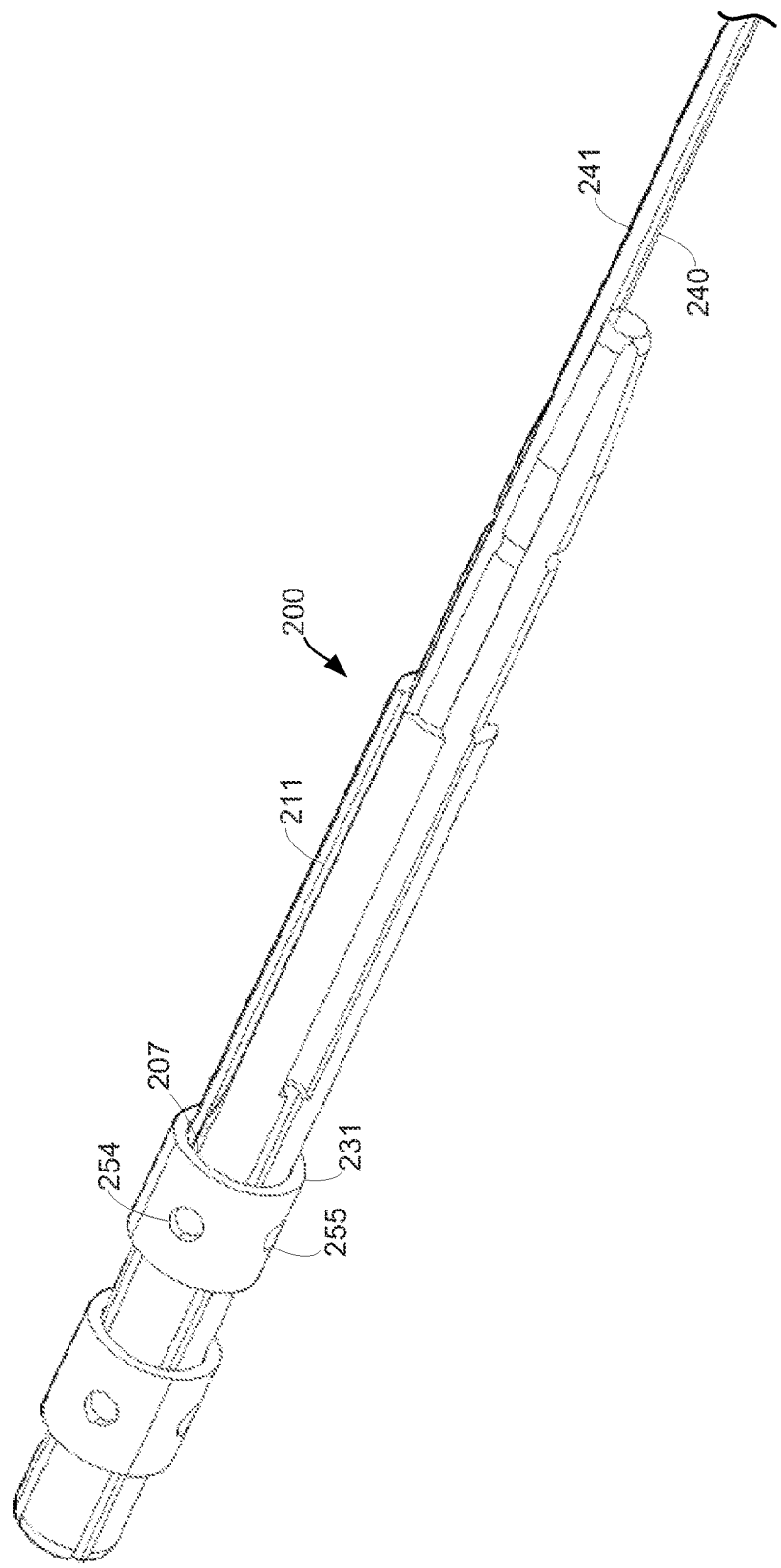
FIG. 6 illustrates a lead end subassembly.

FIG. 6 shows contact ring 231 having been loaded onto the slotted member 200. In particular, a subassembly of the contact ring 231 welded to the crimp sleeve 207, which is crimped to the conductor 241, is slide over the slotted member 200 with the crimp sleeve 207 and conductor 241 sliding within the slot 211. The subassembly of the ring electrode 231, crimp sleeve 207, and conductor 241 is blocked from moving anymore proximally because the positioning feature 221 (shown in FIG. 2) restricts the slot 211, for which crimp sleeve 207 is too large to pass by the positioning feature 221 (as demonstrated in FIG. 5) while the ring electrode 231 surrounds the slotted member 200 and thereby keeps the crimp sleeve 207 within the slot 211. Contact ring 231 includes holes 254 and 255 which can be used for securing the contact ring 231 within an injection mold die and/or for passage of molten polymer fill to fill beneath the contact ring 231.

Figure 7:
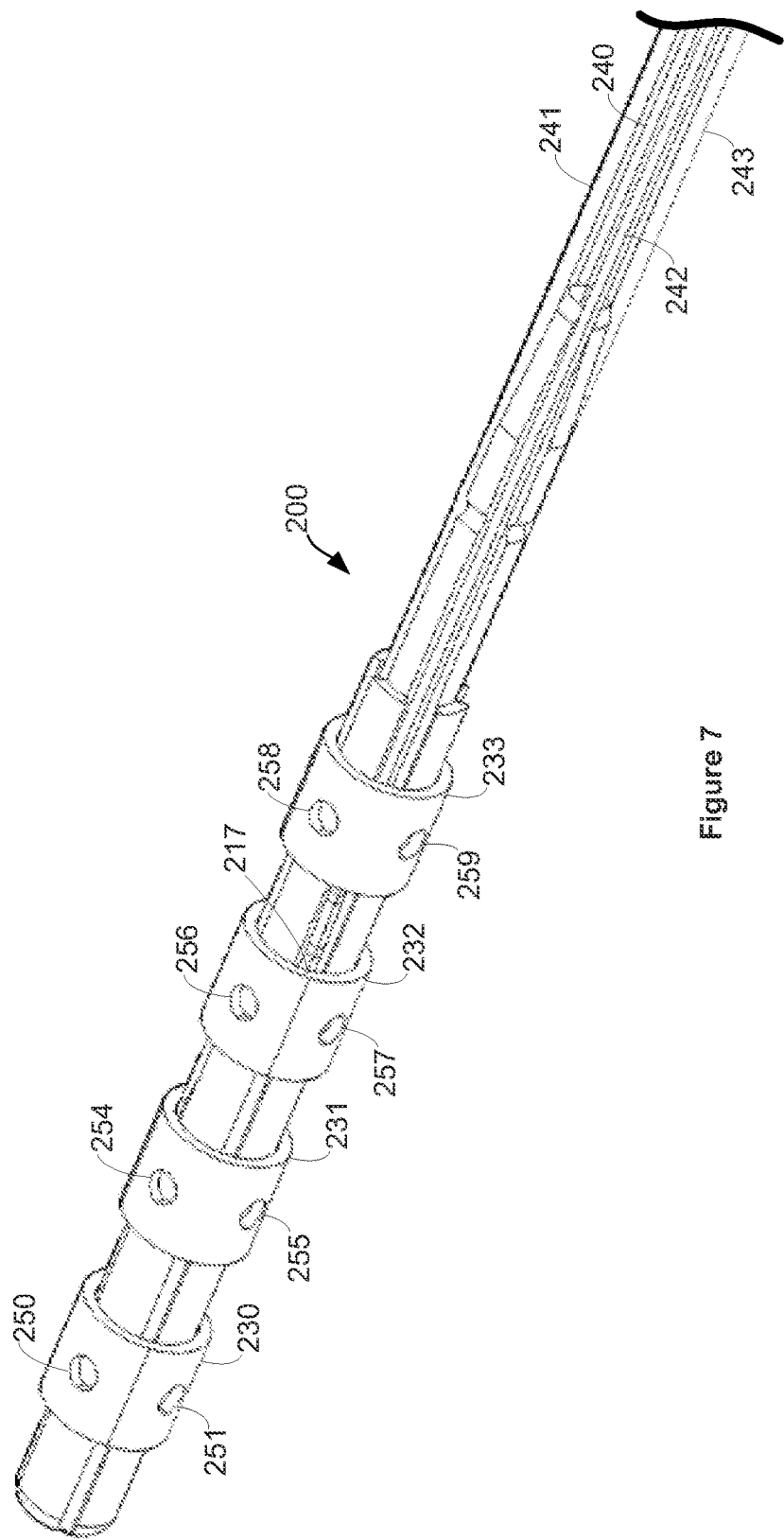
FIG. 7 illustrates a lead end subassembly.

FIG. 7 shows that the slotted member 200 has been fully loaded with four contact rings 230-233. Contact ring 232 is part of a subassembly with crimp sleeve 217 and conductor 242, which are electrically and mechanically combined and then loaded onto the slotted member 200 in the same manner as the subassembly of the contact ring 230, the crimp sleeve 206, and the conductor 240, or in any other manner referenced herein. Likewise, contact ring 233 and conductor 243, coupled by a crimp sleeve (not shown) are loaded onto the slotted member 200. As with contact rings 230 and 231, contact ring 232 has holes 256 and 257 and contact ring 233 has holes 258 and 259.

Figure 8:
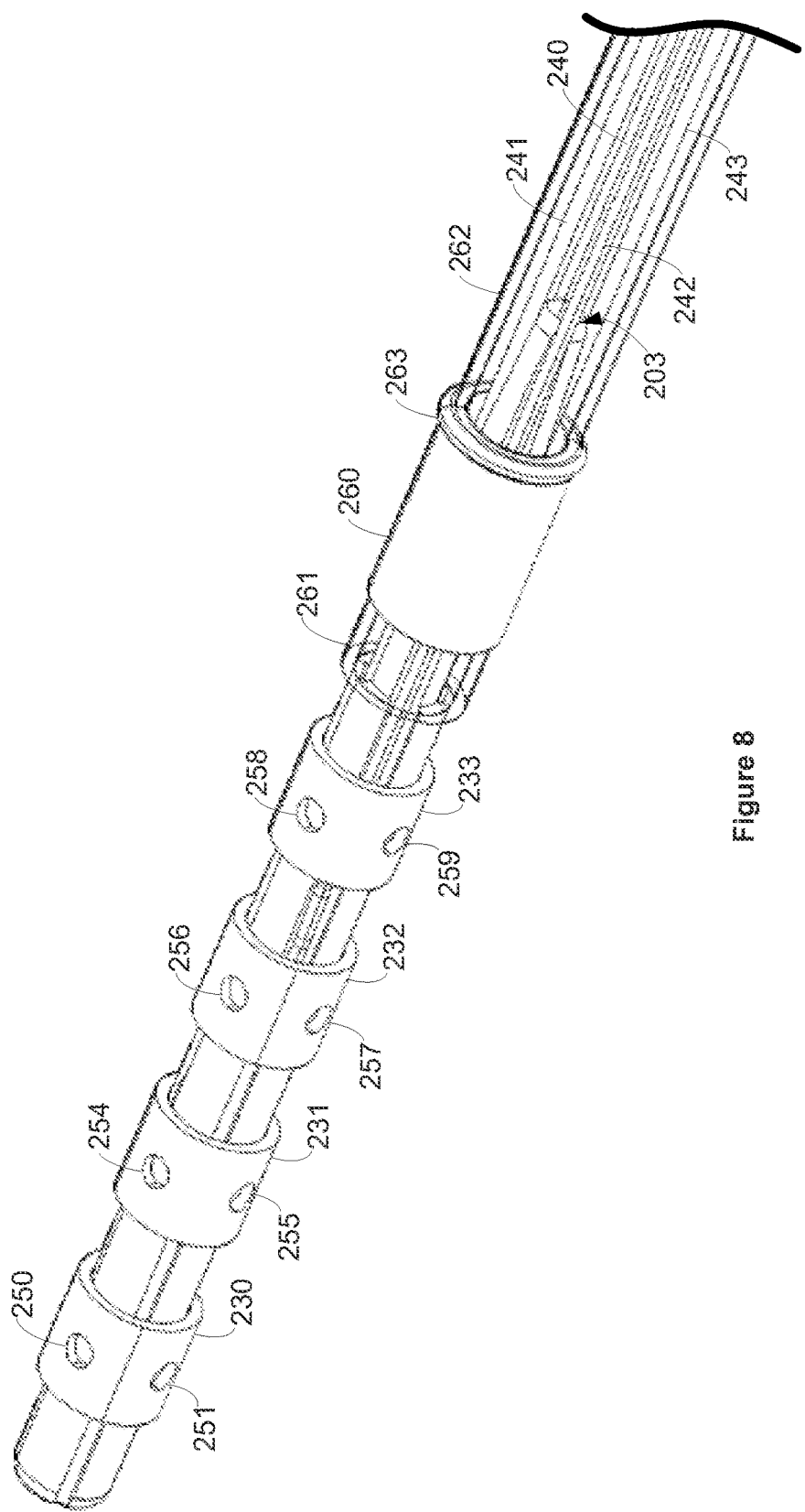
FIG. 8 illustrates a lead end subassembly.

FIG. 8 illustrates a contact 260 having been placed over the distal end of the slotted member 200. As shown in FIG. 8, the conductors 240-243 run through the contact 260 and within the main body tube 262. The main body tube 262 and the conductors 240-243 can run to the distal end of the lead (e.g., the distal end 103 of lead 101). Conductors 240-243 can carry electrical energy along the lead from the contact rings 230-233 to electrical elements on the distal end of the lead (e.g., ring electrodes). The main body tube 262 can, among other things, block bodily fluids from penetrating within the lead wherein the conductors 240-243 are contained.

The contact 260 can be associated with several functions. In some embodiments the contact 260 can be spaced along a proximal end of a lead and be configured to make an electrical connection with an electrical element in a header. The contact 260 can further be connected to a conductor in a lead and electrically connected with an electrode on the distal end of a lead for stimulation and/or sensing, although the contact 260 in the embodiment of FIG. 8 is not connected to a conductor. The contact 260 can additionally or alternatively seal an opening of a header when the proximal end of a lead is inserted into the header. For example, flange 263 may engage with part of an opening of a header to inhibit fluids from entering the opening and penetrating the header. The flange 263 may additionally or alternatively prevent a proximal end of a lead from being inserted too far into a header by engaging with the edge of a header around the header opening.

The contact 260 may also facilitate connecting parts of a lead together. For example, contact 260 is integrated with tube section 261 and main body tube 262. Each of the tube section 261 and the main body tube 262 may be polymer tubes, and are illustrated as transparent in FIG. 8. In some cases, tube section 261 and the main body tube 262 are part of the same tube and the contact 260 is placed over the tube. In some embodiments, each of the tube section 261 and the main body 262 are bonded to proximal and distal surfaces of the contact 260. In some embodiments, the tube section 261 and the contact 260 can be molded separately (e.g., by insert molding around the contact 260) and then adding the subassembly of the tube section 261 and the contact 260 to the rest of the lead being built.

A core pin (not illustrated) can be placed within the lumen of the subassembly shown in FIG. 8. Specifically, a metal pin can be inserted through the lumen 205 of the slotted member 200 at the proximal end 201, past the lumen opening 203, into the enclosed space within the main body tube 262, and through some or the full length of the lumen of the main body tube 262. This subassembly, with the core pin, can be placed within a cavity of an injection mold die (not illustrated). The cavity can define a negative of a cylindrical lead. For example, the cavity can define a negative of the lead proximal end 102 of FIG. 1. The inner diameter of the cavity can be slightly larger than the outer diameter of the contact rings 230-233 and contact 260, sufficient to accommodate the contact rings 230-233 and the contact 260 within the cavity. The inner diameter of the cavity can be small enough to prevent polymer fill from flashing over the contact rings 230-233 or contact 260 by fitting closely over these components.

The injection mold die may contain a pin for each of the contact rings 230-233. The pins can be set within a side of the injection molding die so that holes 250, 254, 256, and 258 are penetrated by the pins when the subassembly shown in FIG. 8 is placed within the injection mold die. The pins can be rigidly attached to the injection mold die, such that the subassembly shown in FIG. 8 is stabilized within the injection mold die to maintain the relative positioning of the elements during the introduction of pressurized molten polymer fill, which might otherwise cause the elements to move relative to one another during the introduction of molten polymer fill under pressure. Nozzles and/or ports of the injection mold die may align with other holes of the contact rings 230-233, such as holes 251, 255, 257, and 259 to facilitate the injection of molten polymer fill into the interior space of the contact rings 230-233. Injecting polymer fill through the interior of the contact rings 230-233 allows the polymer fill to flow outward from the contact rings 230-233, ensuring that the undersides of the contact rings 230-233 are filled with polymer material. It can be advantageous to fill the interior spaces underneath the contact rings 230-233 first because these would be the hardest places to visually insect for air pockets, shot shots, or other undesirable defects if the molten polymer fill was injected elsewhere and the flow fronts of molten polymer fill had to meet underneath the contact rings 230-233.

The alignment of holes (e.g., 250, 254, 256, and 258) with pins means other holes (e.g., 251, 255, 257, and 259) will be aligned with injection ports of an injection mold die. For example, since the holes on a ring are positionally fixed with respect to one another on the ring, and the pins and injection ports of an injection mold die can also be positionally fixed with respect to one another, then alignment of pins with some holes means other holes of the rings will be aligned with the injection ports. Pin alignment can make injection molding of lead ends faster and with fewer alignment errors. However, it is noted that not all embodiments will inject polymer fill through holes of electrical elements, and molten polymer fill may be injected through areas besides holes of electrical elements (e.g., the areas between the contact rings 230-233 of FIG. 8). Moreover, some embodiments may not have any holes in any electrical elements, and accordingly will not align with pins or facilitate the injection of polymer fill.

Although not illustrated in the embodiment of FIG. 8, the contact 260 could have holes in the manner of contact rings 230-233, which could be penetrated to stabilize the position of the contact 260 within the mold during polymer injection by a pin of an injection mold die. Holes not used for matching with a pin could align with a port for injection of polymer fill to the interior space of the contact 260 in the same manner as the contact rings 230-233.

When the die of the injection mold is closed, such as by two plates coming together, molten polymer fill (e.g., polymer resin heated to allow the polymer material to flow) can be injected to fill in the cavity. The polymer fill can fill the entire space of the cavity thereby surrounding many of the components of the subassembly. Once the injection of polymer fill is complete, the die can be cooled, the polymer material solidifying as it cools. The subassembly can then be removed from the injection molding die. Gates from injection molding can be cut from the subassembly. Cutting gates may include cutting polymer fill along the holes 251, 255, 257, and 259 flush with the exterior surface of the contact rings 230-233 to provide a smooth surface along the lead end.

As shown in FIG. 8, alignment of contact rings 230-233 by engagement with positioning features of the slotted member 200 provides for an array of contact rings 230-233 evenly spaced along the slotted member 200. Specifically, the array of contact rings 230-233 has consistent spacing between the contact rings 230-213 and angular alignment of the holes 250-254-256-258 and 251-255-257-259. Also, FIG. 8 shows that the contact rings 230-233 are axially aligned with each other, the slotted member 200, and the contact 260. In particular, contact rings 230-233 are axially aligned because each is placed over the slotted member 200. There is some clearance between the inner surfaces of the contact rings 230-233 and the outer surface of the slotted member 200. Enough clearance is provided to allow the contact rings 230-233 to slide over the circular slotted member 200. In some cases this clearance also allows polymer fill to penetrate and fill the space between the inner surfaces of the contact rings 230-233 and the outer surface of slotted member 200, as will be later described. In various embodiments, the clearance between the inner surfaces of the contact rings 230-233 and the outer surface of slotted member 200 is small enough to keep the contact rings 230-233 substantially axially aligned with each other and the slotted member 200 by some contact between the inner surfaces of the contact rings 230-233 and the outer surface of the slotted member 200. Axially aligned contact rings 230-233 provide a consistent and smaller profile for plugging a proximal lead end into an opening of a header. Moreover, axially aligned contact rings 230-233 can provided for tighter tolerances with seals of the header to keep fluids out of the header and from further penetrating between contact rings within the header.

Figure 9:
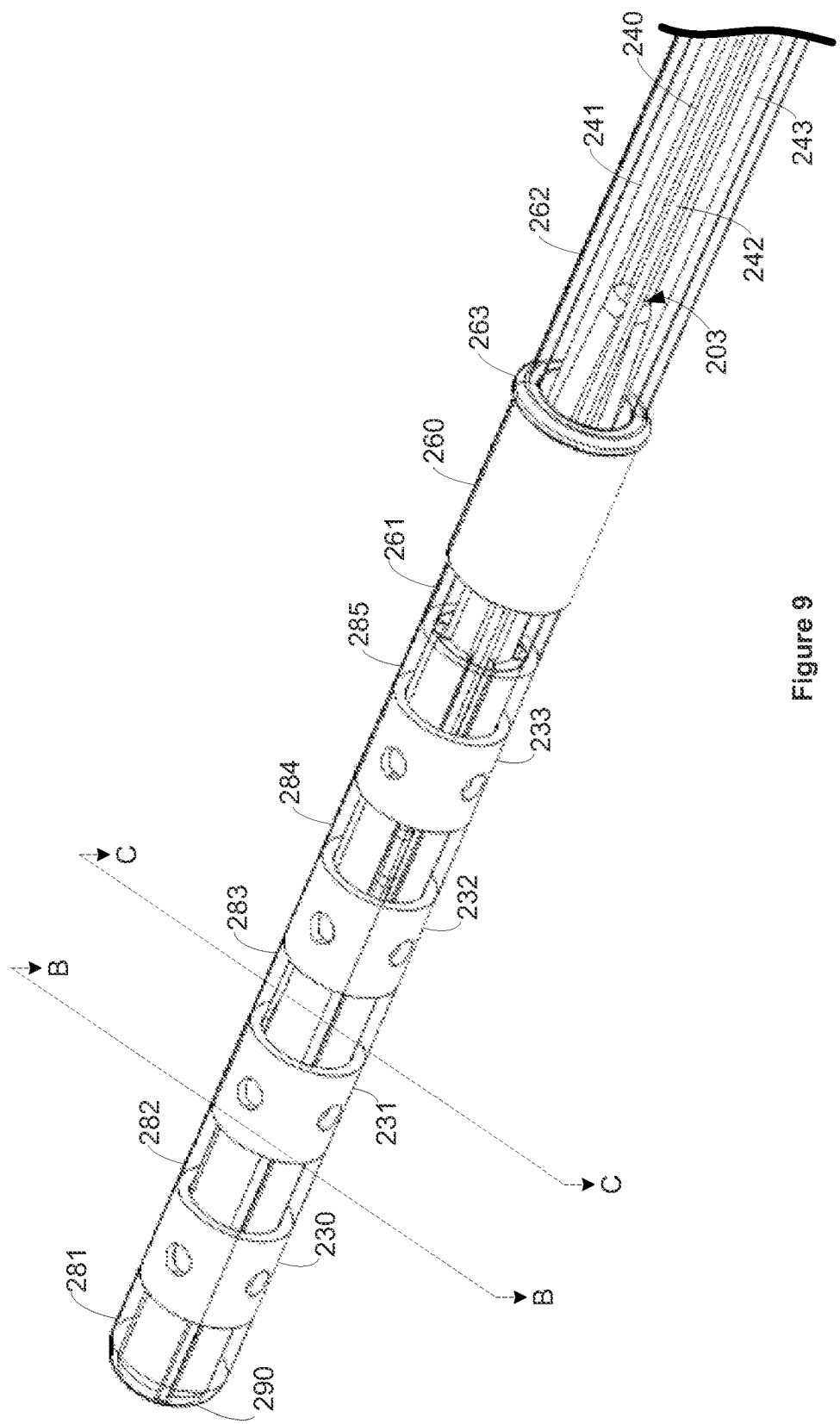
FIG. 9 illustrates a lead end.

FIG. 9 it illustrates a proximal end of a lead following injection molding as described above and after removal of the core pin. The interior space of the injection mold cavity has been filled with now solid polymer fill. Some areas of the conductors 240-243 can be encapsulated by the polymer fill, such as the areas of the conductors 240-243 underneath the contact rings 231-233 and the contact 260. The slots 210-213 can also be partially or fully filled with polymer fill. Also, the spaces between the contact rings 230-233 have been filled in with polymer fill. As a result, polymer sections 281-285 have been formed from the inner surface of the die cavity, forming a cylindrical shape that spans between the contact rings 230-233. The outer diameter of each of the polymer sections 281-285 is substantially the same as the outer diameter of the contact rings 230-233. As such, each of the contact rings 230-233 is in direct contact with polymer sections 281-285 proximally and distally. The contact rings 230-233 being surrounded proximally and distally by the polymer sections 281-285 fixes the contact rings 230-233, including fixing the axial alignment and spacing between the contact rings 230-233.

Figure 10:
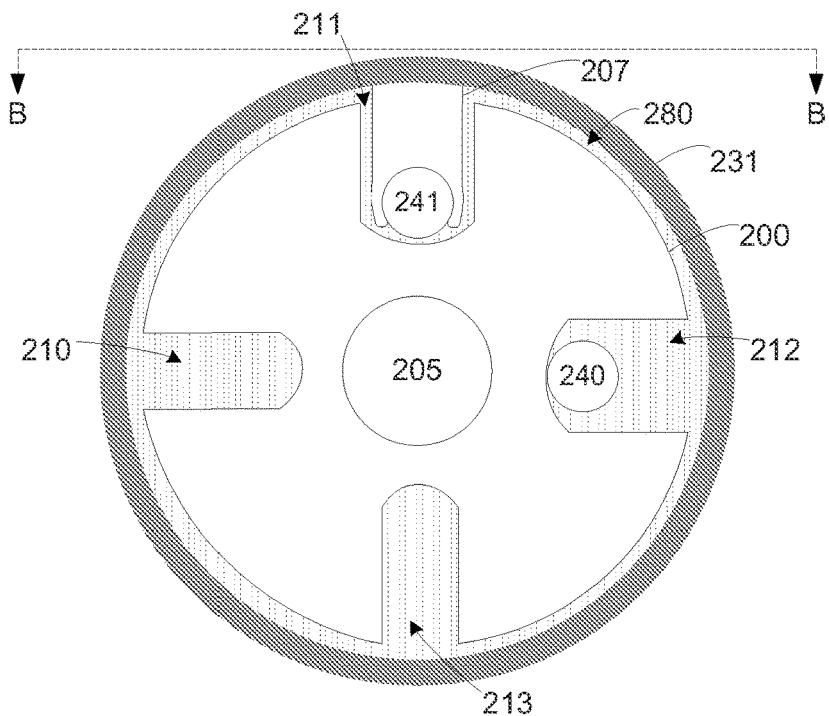
FIG. 10 illustrates a cross sectional view of lead end.

A rounded proximal end 290 has also been made from the injection molding process. The rounded proximal end 290 can be made from polymer fill. The end of the lead may be left open, as shown in FIG. 10, to allow access to the lumen 205 of the lead, or it may be closed off, such as during injection molding or with a plug. The polymer fill of polymer section 285 can melt and bond with the polymer of tube section 261 to make the exterior of the lead end continuous and seamless between the polymer section 285 and the tube section 261.

The polymer fill can encapsulate at least part of the slotted member 200, mechanically fixing the slotted member 200 to the other portions of the lead, including the contact rings 230-233. In some embodiments the polymer fill will further melt or otherwise chemically bond with the polymer material of the slotted member 200, however not all embodiments of this disclosure are so limited.

The polymer fill acts as a web of material that is mechanically attached to the components of the lead end by surrounding some or all of the component surfaces. For example, the polymer fill spans underneath each of the contact rings 230-233 to bridge between each of the polymer sections 281-285. In various embodiments, the polymer fill will be continuous from the proximal end of the slotted member 200 to the distal end of the slotted member 200, thereby fixing the components around the slotted member 200 and making a robust lead end. In some embodiments, the polymer fill will extend distal of the lumen opening 203. In such cases, the core pin in the lumen 205 may extend beyond the point to which the polymer material will flow during injection molding to maintain the lumen 205.

The slotted member 200 adds stiffening strength to the lead end and the polymer fill mechanically binds the components of the lead end while also insulating various components. The section of a lead containing slotted member 200, such as the lead proximal end 102 of FIG. 1, can be stiffer than the main body of the lead because of the presence of the slotted member 200. In this way, the slotted member 200 can add stiffness to a section of a lead where it is needed while leaving the remainder of a lead, such as a main body, flexible for conforming to an implant path in the body and moving with the body. In various embodiments the section of the lead containing the slotted member 200 can still flex but will be stiffer then the sections of the lead that do not have a slotted member 200.

A particularly stiff proximal end of the lead may be useful in inserting the proximal end into a header, in case an initial misalignment causes the proximal end to bend while the physician pushes the proximal end. It is noted that the slotted member 200 may be substantially stiffer than conductors (e.g., cables, filers, coils, or other elongated conductive elements) within the lead. As such, in various embodiments, the stiffness of a lead end comes predominantly from the slotted member 200 as compared to the stiffening contributions of other longitudinally extending components of the lead end.

The polymer fill can be transparent. As shown in FIG. 9, the slotted member 200 can still be seen beneath the polymer fill forming the polymer sections 281-285. The polymer fill material may be, for example, opaque, colored, transparent, or non-transparent. The polymer fill may be polyether ether ketone (PEEK), polysulfone, urethane, and/or silicone, among other material types. In some cases epoxies or other adhesives or materials may be used in place of polymer fill to fill in the lead end.

Slots 210-213 of the slotted member 200 can serve as areas for the polymer fill to mechanically attach to the slotted member 200 by filling in the slots 210-213 and further surrounding the periphery of the slotted member 200. This can occur in the spaces immediately distal and proximal of each of the contact rings 230-233, such as at each of the polymer sections 281-285. In this way, each of the contact rings 230-233 is immediately surrounded distally and proximally by two of the polymer sections 281-285. Being that the polymer sections 281-285 can themselves be mechanically fixed to the slotted member 200 by surrounding the slotted member 200 and filling in the slots 210-213, these polymer sections 281-285 can prevent the contact rings 230-233 from moving and maintain the positioning and relative spacing of the contact rings 230-233. It is noted that the slotted member provides spaces distally and proximally of all of the proximal end contact rings 230-233 where the polymer sections 281 and 285 are located, which can sandwich the array of contact rings 230-233.

Figure 11:
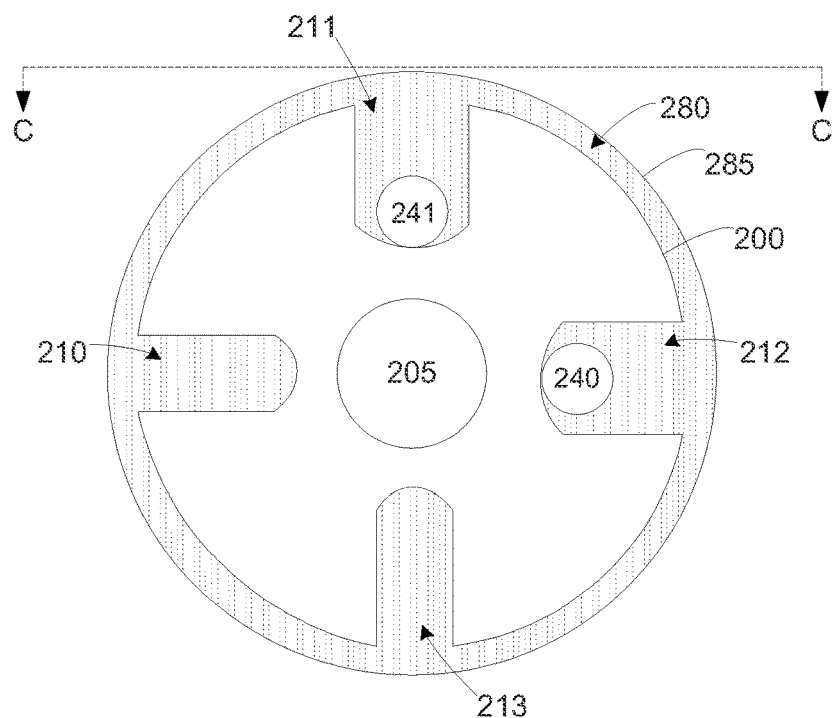
FIG. 11 illustrates a cross sectional view of a lead end.

FIGS. 10 and 11 illustrate BB and CC cross sections of FIG. 9, respectively. FIG. 10 shows the BB cross section slice that is taken through the contact ring 231 and slotted member 200. Polymer fill 280 is shown by vertical hash marks. As shown in FIG. 10, the polymer fill 280 surrounds each of the conductors 240 and 241, is within the slots 210-213 of the slotted member 200, surrounds the slotted member 200, and is between the outer surface of the slotted member 200 and the inner surface of the contact ring 231. In various embodiments, one or more of the conductors 240 and 241 for other conductor) is not fully surrounded by the polymer fill 280 as the conductors may be pressed against the bottom or sidewall of slots 211 and 212. However, in some embodiments one or more conductors may be encapsulated by polymer fill 280 for at least some length along the lead end. In various embodiments, a slotted member 200 may be encapsulated (e.g., surrounded by polymer fill 280 as shown in FIGS. 10 and 11) by polymer fill 280 for its entire length. In various other embodiments, a slotted member 200 may be encapsulated by polymer fill 280 for only a limited portion of its length.

The top of the crimp sleeve 207 is shown welded to the inside of the contact ring 231 while the polymer fill 280 contacts the sides and bottom of the crimp sleeve 207.

FIG. 11 shows the CC cross section slice that is taken through the polymer section 283 of FIG. 9, and as such the outer surface 285 of the lead end is defined by polymer fill 280. As shown in FIG. 11, the outer surface 285 of the polymer fill 280 takes on a circular shape, which is the same shape of the injection mold cavity negative. Other shapes, such as ovals and non-rounded shapes having one or more flat sections such as a paddle, square, or rectangle shape are also contemplated.

As shown in FIG. 11, conductors 240 and 241 are pushed against the bottoms of slots 212 and 211. In various embodiments, the polymer fill 280 is injected through holes (e.g., 255) in the contact rings (e.g., 231). As such, the flow of the molten polymer fill is from the periphery towards the center, following an outside-in path. This flow of polymer fill can push the conductors 240 and 241 down within the slots 212 and 211, where the conductors 240 and 241 will remain if the polymer fill 280 is cooled in that position. It is noted that flowing polymer fill can push the conductors 240 and 241 down within the slots 212 and 211 in some configurations where holes are not used as injection ports. It can be adventurous in some embodiments to have conductors low within the slots as this provides the most clearance between each conductor and the top of the slot and the exterior of the lead. As this space is filled with insulating polymer fill 280 in many embodiments, the further separation provides more insulating polymer fill 280 between the conductors and the exterior of the lead to protect the conductors 240 and 241 from breaches in the lead, gouges, or other damage that could compromise the electrical isolation of the conductors 240 and 241.

A lumen 205 may be maintained within slotted member 200 by the core pin during injection molding, however not all embodiments may have a lumen 205 and the slotted member 200 may have a solid middle. The lumen 205 may accommodate guide wires, stylets, and other elongated objects which can be placed within the lead. As shown in FIG. 9, the conductors 240-243 are spread around the lumen opening 203 by the slotted member 200 as the slots 210-233 containing the conductors 240-243 are on the periphery of the slotted member 200 while the lumen opening 203 is in the center of the slotted member 200. Therefore, a stylet or other object could be extended distal of the lumen opening 203 and further through the lead while the slotted member 200 maintains at least some separation between the stylet or other object and the conductors 240-243 for at least some length of the lead.

In some embodiments the slotted member 200 is made from a radiopaque material. Such embodiments may have particular advantages where a radiopaque slotted member 200 is used to construct a distal end of a lead. The radiopaque slotted member 200 could be seen underneath the skin using medical imaging. The radiopaque slotted member 200 would be fully insulated within the lead end by polymer fill 280 and the other components of the lead as described herein which can avoid having the radiopaque material be biocompatible for directly contacting bodily tissue.

In some embodiments, the distal end or other part of the slotted member 200, the contact 260, and/or the flange 263 can be longitudinally spaced to align with a feature of an IMD during insertion of a lead proximal end into a head. The feature of the IMD may be the end of the IMD or an opening of a header. Such alignment can serve as in indicator to a physician showing when the proximal lead has been fully inserted into a header opening. Such an indicator can provide assurance that a proximal end has been fully inserted into a header opening while minimizing further pushing by the physician once the proximal end is fully inserted. The distal end or other part of the slotted member 200, the contact 260, and/or the flange 263 can be colored differently than the rest of the lead to distinguish it as an insertion indicator. In some embodiments, the slotted member 200 can be seen through a main body tubing 262 or felt as a stiff section within the lead by a physician when serving as an insertion indicator. The slotted member 200 can be colored differently than the rest of the lead to serve as a distinguishing indicator. In some embodiments the slotted member 200 will disappear into the header opening as an indication that the lead proximal end has been fully inserted into the header.

Each conductor 240-243 can be an individual metal filar, cable, or coil, for example. Each conductor 240-243 can be made of metal or other conductive material and can be configured to conduct electrical energy (e.g., stimulation pulses and/or bioelectrical signals) along a lead. Each conductor can further be coated (e.g., with polytetrafluoroethylene (PTFE), polyimide, or other insulator) to insulate the conductive metal to prevent electrical shorting.

Each of the conductors can be cut to a different length. The different lengths can correspond to which electrical elements the conductors will be respectively connected. For example, the length to which the conductors 240-243 are cut can be based on with which contact ring 230-233 it is to be connected and/or based on in which slots 220-223 the conductors will be placed. As shown in FIG. 2, the positioning features 220 and 221 are at different longitudinal lengths along the slotted member 200, and as such conductors 240-243 can be cut to different lengths to match these positions of the positioning features 220 and 221 (or other positioning features).

Contact rings 230-233 are electrical elements. While contact rings 230-233 are shown as being loaded onto the slotted member 200 in FIGS. 3-7, other electrical elements can additionally or alternatively be loaded onto the slotted member 200. An electrical element, as used herein, refers to an electrically conductive component exposed on a lead and configured to deliver and/or receive electrical energy. Electrical elements can be any type of electrode, including rings and segmented electrodes. A segmented electrode refers to an electrode that only spans around a limited portion of the circumference of a lead, and in some cases multiple segmented electrodes (e.g., three) are arrayed around the same circumference of a section of a lead. Segmented electrodes, or other electrodes, may have features such as projections on their underside to engage with slots, where injected polymer fill can encapsulate the features to mechanically attach the segmented electrode to the slotted member and the rest of the lead.

FIG. 12 illustrates a flow chart of a method 300 for making a lead end. The method 300 can correspond to the steps described and illustrated in connection with FIGS. 1-11, for example. The method 300 includes connecting 310 a plurality of elongated electrical conductors to a plurality of electrical elements. The plurality of elongated electrical conductors may correspond to the conductors 240-243 of FIG. 7, for example, or other conductors. The conductors can be filers, cables, coils, or any other elongated conductive component for conducting electrical signals. The conductors can be long enough to run the length of a lead body and thin enough to be contained in slots and run through the interior space of the main tube body.

The electrical elements used in the method 300 or elsewhere herein can be any type of electrode and/or contact, such as a contact ring, electrode ring, or a segmented electrode, for example. The plurality of electrical elements may correspond to the contact rings 230-233 of FIG. 7, although other electrical elements are also contemplated, such as partial rings or segmented electrodes.

Connecting 310 conductors and electrical elements can include welding a conductor to a respective electrical element such that each electrical element is mechanically and electrically connected to a different conductor. Other techniques for mechanically and electrically connecting conductors to electrical elements are also contemplated, such as a mechanical crimp around a conductor, pinching a conductor between parts of an electrical element, or other technique for making a mechanical and electrical connection between a conductor and an electrical element.

Connecting 310 may involve the direct connection of conductors to electrical elements such as by welding, while in some other embodiments a coupling feature may be used as an intermediary. In various embodiments, connecting 310 may include welding a coupling feature (e.g., a crimp sleeve as in FIG. 4) to the edge or underside of an electrical element (e.g., a distal or proximal edge of a ring, a slot within the ring, or an inner surface of the ring). Connecting 310 may further include connecting the coupling feature to a conductor, such as crimping a crimp sleeve over the conductor. In some cases, connecting 310 the plurality of elongated electrical conductors to the plurality of electrical elements may make subassemblies of conductors joined to electrodes, which may be used at a later time to complete the steps of the method 300.

The method 300 further includes loading 320 one of the conductors connected to one of the electrical elements onto a slotted member. The slotted member can be any slotted member referenced herein, such as slotted member 200. The electrical element and the conductor (and the coupling feature if used) may be slid along the slotted member to position 330 the conductor and the electrical element along the slotted member based on a positioning feature within the slot. The positioning feature may be a restriction of the slot, termination of the slot, a bump in the slot, or other blocking obstruction at least partially within the slot, in some cases, the electrical element and the conductor (and the coupling feature if used) may be slid as a subassembly along the slotted member until one of the components of the subassembly engages with the position feature. Engagement may include the position feature physically blocking one or more components of the subassembly of the conductor, electrical element, and/or coupling feature from sliding any further along the slotted member and/or within the slot.

As indicated in the method 300, the steps of loading 320 a conductor connected to one of the electrical elements and positioning 330 the electrical element can be repeated for each of the plurality of electrical elements connected 310 to the plurality of conductors until all of the electrical elements connected 310 to respective conductors are loaded 320 onto the slotted member and positioned 330 at respective positions along the slotted member.

The use of a slotted member with a plurality of slots arrayed around the circumference of the slotted member eases assembly of a lead because the electrical elements can be properly positioned 330 in predetermined angular and longitudinal positions by running the subassemblies along the slotted member until the movement is opposed by a positioning feature. For example, an assembler can place a plurality of subassemblies on a slotted member and run each subassembly along a slot until the movement of each subassembly is blocked. Particular longitudinal positions of electrical elements can be achieved and assured based on the resistance to further sliding. As such, electrical elements can be evenly spaced along the slotted member without further measuring or checking of the relative positions. Further, particular angular orientations of the electrical elements can be achieved and assured based on the tracking of components of a subassembly within a slot. Holes of the electrical elements can be spaced and orientated along the slotted member in this manner for later matching with pins and/or polymer fill ports for injection molding.

The method 300 further includes injecting 340 polymer fill to contact and cover at least a portion of the slotted member and define an exterior surface of a lead body. An exterior surface of a lead body can be defined by the injected polymer fill and exposed portions of the plurality of electrical elements, such as alternating polymer sections and metal rings defining an end of a lead. In this way, some parts or the entire slotted member can be encapsulated by polymer fill, thereby mechanically gripping the slotted member and mechanically attaching the slotted member to other components of the lead fixed by the polymer fill.

Although various embodiments described herein concern the use of injection molding, various embodiments may additionally or alternatively use a reflow process. Polymer cuffs can be loaded onto a slotted member. The polymer cuffs can correspond to the polymer sections 281-285 of FIG. 9. The polymer cuffs can be loaded onto the slotted member alternating with electrical elements (e.g., contact rings) or could be slit and put on the slotted member after all of the electrical elements have been loaded onto the slotted member. A shrink tube can then be placed over the polymer cuffs and the shrink tube heated (e.g., by a heat element or blowing hot air over the shrink tube). The shrink tube can shrink in response to the heat, applying pressure to the polymer cuffs while also transferring heat to the polymer cuffs. The polymer material can then flow around the slotted member. It is noted that this technique may be used without polymer cuffs following an injection molding process (e.g., to the embodiment of FIG. 9) to smooth any edges.

Although the use of a slotted member in the construction of a lead proximal end is used in many of the examples herein, it is noted that the same or similar construction techniques can be used to build a lead distal end using a slotted member. For example, the technique of using slotted member 200 in FIGS. 2-12 to build a lead end can be used to build either a lead proximal and/or distal end. In the case of building a lead distal end, the contact 260 may be replaced by another ring electrode or be absent. It is also noted that the number of electrical elements illustrated in the various Figures is not intended to limit the number of electrical elements on a lead end constructed around a slotted member. One, two, three, four, eight, ten, sixteen, or any other number of electrical elements can be placed on a lead end using the techniques discussed herein.

Although the examples presented herein generally describe a single lead to conduct electrical energy between an IMD and tissue, multiple leads may be used in accordance with the devices and methods of the present disclosure. In some cases, multiple leads are used in parallel, where the multiple leads respectively connect to one IMD. In some cases, multiple leads are connected serially, where at least one of the leads serves as a lead extension. It is noted that the devices and methods presented herein are applicable to lead extensions and other leads that bridge electrical connections. For example, the construction of a proximal end and/or a distal end of a lead extension could be done in accordance with the present disclosure (e.g., having a slotted member), where the proximal end plugs into an IMD and the distal end mechanically and electrically connects with another lead. The distal and/or proximal ends of the lead mechanically and electrically connected with the lead extension can additionally or alternatively be constructed in accordance with the present disclosure (e.g., having a slotted member).

The various techniques, features, and components discussed herein in various embodiments are applicable to various other embodiments in different configurations and combinations, as the present disclosure makes use of examples to illustrate options which are not limited to the specific embodiments presented. The present disclosure is presented using examples to illustrate and describe various aspects of a lead end having a spine. Each example and set of examples are presented herein to exemplify various features and options. As such, each example embodiment should be understood to be selectively combinable and modifiable in view of the other embodiments presented herein. The specific examples and options are therefore described in a broadening sense and not in a limiting sense.

We claim:

1. A lead, the lead comprising:
   a first end, a second end, and a main body between the first end and the second end, the first end having a first plurality of exposed electrical elements and the second end having a second plurality of exposed electrical elements;
   a slotted member within the first end, the slotted member having a length and being longitudinally elongated along the length, the slotted member having a plurality of slots extending along at least a portion of the length of the slotted member and further having a plurality of positioning features, each slot defining a respective positioning feature of the plurality of positioning features, each of the plurality of positioning features located at different longitudinal positions along the length of the slotted member; and
   a plurality of conductors at least partially within the plurality of slots, each slot of the plurality of slots containing at least a respective one of the plurality of conductors, the plurality of conductors electrically connecting at least some of the exposed electrical elements of the first plurality to at least some of the exposed electrical elements of the second plurality.

2. The lead of claim 1, wherein the plurality of slots are arrayed around the circumference of the slotted member.

3. The lead of claim 1, wherein the plurality of slots are evenly spaced from each other around the circumference of the slotted member.

4. The lead of claim 1, wherein a plurality of crimp sleeves connect the plurality of conductors to the first plurality of exposed electrical elements, the plurality of crimp sleeves at least partially within the plurality of slots.

5. The lead of claim 1, wherein the slotted member is tapered distally of the plurality of slots.

6. The lead of claim 1 wherein the first end further comprises polymer fill encapsulating at least a portion of the slotted member, the polymer fill within at least some portions of the plurality of slots, the polymer fill deposited by injection molding.

7. The lead of claim 6, wherein the polymer fill defines at least some of the exterior surface of the first end between the exposed electrical elements of the first end.

8. The lead of claim 6, wherein each exposed electrical element of the first end comprises a ring that defines at least some of the exterior surface of the first end.

9. The lead of claim 8, wherein each ring of the first end comprises multiple holes through the exterior of the ring to the interior of the ring, the polymer fill at least partially within one of the holes.

10. The lead of claim 9, wherein the holes are dimensioned to accommodate a pin of an injection molding die, engagement of the pin with the hole securing the ring within the injection molding die during injection of the polymer fill.

11. The lead of claim 1, wherein the first end is configured to plug into an implantable medical device and the exposed electrical elements of the first end are spaced to electrically connect with respective channels of the implantable medical device.

12. The lead of claim 1, wherein the slotted member provides a majority of the axial strength of the first end.

13. The lead of claim 1, further comprising a lumen within the first end and the main body, the lumen extending within the slotted member and open on the first end of the lead.

\* \* \* \* \*